(12) United States Patent
Saliya et al.

(10) Patent No.: US 8,643,830 B2
(45) Date of Patent: Feb. 4, 2014

(54) PROCESS FOR PREDICTING METALLIC GLOSS OF COATING RESULTING FROM COATING COMPOSITIONS BY WET COLOR MEASUREMENT

(71) Applicant: Axalta Coating Systems IP Co., Wilmington, DE (US)

(72) Inventors: Rajesh Gopalan Saliya, Philadelphia, PA (US); Ayumu Yokoyama, Wallingford, PA (US); Anthony Moy, Garnet Valley, PA (US)

(73) Assignee: Axalta Coating Systems IP Co., LLC, Wilmington, DE (US)

( * ) Notice: Subject to any disclaimer, the term of this patent is extended or adjusted under 35 U.S.C. 154(b) by 0 days.

(21) Appl. No.: 13/666,552

(22) Filed: Nov. 1, 2012

(65) Prior Publication Data

US 2013/0141713 A1    Jun. 6, 2013

Related U.S. Application Data

(60) Provisional application No. 61/554,050, filed on Nov. 1, 2011.

(51) Int. Cl.
*G01N 1/00*       (2006.01)
*G01N 21/55*      (2006.01)

(52) U.S. Cl.
USPC .............................................. 356/36; 356/445

(58) Field of Classification Search
USPC ............................................................ 356/36
See application file for complete search history.

(56) References Cited

U.S. PATENT DOCUMENTS

| | | | |
|---|---|---|---|
| 2013/0107266 A1* | 5/2013 | Moy et al. | 356/445 |
| 2013/0141724 A1* | 6/2013 | Yokoyama et al. | 356/402 |

* cited by examiner

*Primary Examiner* — Roy M Punnoose
(74) *Attorney, Agent, or Firm* — Ingrassia Fisher & Lorenz, P.C.

(57) ABSTRACT

The present process adjusts the amount of flattener added to the coating composition, the gloss of a coating resulting therefrom can be controlled from glossy to flat (matte) finish. The process includes measuring reflectance (L-value) of a layer of the coating composition applied over a test substrate by using gloss prediction device of the present invention. The metallic gloss of a coating resulting from the layer is then measured. The process is repeated with varying amounts of one or more flatteners added to the composition and the metallic gloss vs. reflectance is plotted on a graph. Then by means of a curve fitting equation, a metallic gloss prediction curve is plotted. By measuring the reflectance of a wet layer of a target coating composition, the metallic gloss that would be produced by a coating from that target coating composition can then be predicted by using the gloss prediction curve.

14 Claims, 3 Drawing Sheets

PROCESS FOR PREDICTING METALLIC GLOSS OF COATING RESULTING FROM COATING COMPOSITIONS BY WET COLOR MEASUREMENT

CROSS-REFERENCE TO RELATED APPLICATION

This application claims priority under 35 U.S.C. §119 from U.S. Provisional Application Ser. No. 61/554,050, filed Nov. 1, 2011, which is hereby incorporated by referenced in its entirety.

FIELD OF INVENTION

The present invention is directed to a process of predicting the metallic gloss of a coating that results from a layer of a coating composition applied over a substrate, wherein said coating composition contains metallic flakes. The process is more particularly directed to a quality assurance process that predicts on a real time basis the metallic gloss of coatings that would result from automotive OEM and refinish paints while such paints are being manufactured.

BACKGROUND OF INVENTION

Depending on the end use of a coating composition in automotive applications, such as that applied over an auto body versus that applied over a car bumper, the metallic gloss provided by flakes is typically adjusted by adding additives to the composition, such as flatteners to reduce the gloss. The higher the amount of flattener in a coating composition, the lower will be the metallic gloss of a coating resulting therefrom and vice versa. Thus, paint manufacturer typically checks a sample of a coating composition, such as automotive OEM paint or refinish paint, while it is being made to determine the metallic gloss of a coating that would result from it. Therefore, from time to time, an aliquot of such coating compositions being manufactured is taken, applied as a layer of desired thickness over a test substrate, dried and/or cured into a coating and its gloss measured to check whether the gloss is in a desired gloss range. The process parameters are then adjusted and the aforedescribed testing procedure is repeated until the adjusted coating composition falls within a desired gloss range.

The aforementioned testing procedure is not only time consuming and cumbersome but it also results in frequent interruptions in the manufacturing process. As a result, the batch-to-batch quality of the resulting coating compositions can be detrimentally affected. Therefore, a need exists to develop a process that could predict the gloss of a coating that would result from a coating composition while it is still being manufactured such that the manufacturing process could be readily adjusted on a real time basis to get the desired metallic gloss.

STATEMENT OF INVENTION

The present invention is directed to a metallic gloss prediction process comprising:

(a) dispensing on a test substrate a $L_0$ layer of a substantially uniform thickness of a $S_0$ coating composition containing metallic flakes through a vessel of a metallic gloss prediction device containing said coating composition;

(b) projecting on said $L_0$ layer a beam of light of a preset intensity at a preset angle of incidence from a light source;

(c) measuring $B_0$ reflectance of said beam reflected from said $L_0$ layer at a preset angle of reflectance by an optical measurement instrument;

(d) curing or drying said $L_0$ layer into a $C_0$ coating;

(e) measuring $Y_0$ metallic gloss of said $C_0$ coating at a preset metallic gloss angle by a gloss meter;

(f) storing said $B_0$ reflectance of said $L_0$ layer and said $Y_0$ metallic gloss of said $C_0$ coating in a computer usable storage medium of a computer;

(g) repeating said steps (a) through (f) for $S_1$ to $S_n$ coating compositions respectively comprising $F_1$ to $F_n$ parts by weight of one or more flatting agents based on 100 parts by weight of said coating composition to determine $B_1$ to $B_n$ reflectance of $L_1$ to $L_n$ layers and $Y_1$ to $Y_n$ metallic gloss of $C_1$ to $C_n$ coatings wherein n ranges from 4 to 20;

(h) locating intersecting points on a graph where said $B_0$ to $B_n$ of said $L_0$ to $L_n$ layers on X-axis of said graph intersect with said $Y_0$ to $Y_n$ metallic gloss of said $C_0$ to $C_n$ coatings on Y-axis of said graph;

(i) using a curve fitting equation to produce a metallic gloss prediction curve on said graph;

(j) dispensing on said test substrate a $L_T$ layer of said substantially uniform thickness of a target coating composition through said vessel of said metallic gloss prediction device containing said target coating composition further comprising said flatting agent;

(k) projecting on said $L_T$ layer a beam of light at said preset intensity and at said preset angle of incidence from said light source;

(l) measuring $B_T$ reflectance of said beam reflected from said $L_T$ layer at said preset angle of reflectance by said optical measurement device;

(m) locating said $B_T$ of said $L_T$ layer on said X-axis of said graph;

(n) locating an intersecting point on said metallic gloss prediction curve that intersects with said $B_T$ on said X-axis of said graph; and (o) predicting metallic gloss at said preset metallic gloss angle of a target coating resulting from said target layer by locating $Y_T$ on said Y-axis of said graph that intersects with said intersecting point on said metallic gloss prediction curve that intersects with said $B_T$ on said X-axis of said graph.

DETAILED DESCRIPTION OF PREFERRED THE EMBODIMENT

As defined herein:

"Flakes" means conventional metallic flakes, such as aluminum flakes used in coating compositions that exhibit gloss. Flakes can also include conventional mica flakes, inorganic flakes, organic flakes or a combination thereof.

"Coating composition" means a coating composition that contains one or more types of flakes that provide lustrous appearance, i.e., gloss, to a coating composition applied over a substrate, such as an automotive body, bumper or a fender. By "gloss" is meant the visual change in brightness or lightness of the flake, such as metallic aluminum flake, with a change in viewing angle, that is, a change from 90 degrees to 180 degrees. The greater the visual change from light to dark appearance, the better the gloss. The gloss accentuates the lines and curves of an automobile; therefore, it is very important in achieving this sought-after appearance of the coating. Automotive coating compositions containing metallic flakes, such as aluminum flakes are generally utilized to obtain the highly sought after metallic glossy lustrous appearance. The gloss can be controlled by adding an additive such as, a TU09-GC01 flattener supplied by DuPont Company of Wilmington, Del. to a coating composition to impart glossy (no flattner), semi-glossy or flat appearance to a coating resulting therefrom by suitably increasing or decreasing the amount of flattner added to the coating composition containing metallic flakes. While producing a coating composition, various components of a coating composition, such as pigments, flakes, binder polymers, solvents, etc, are mixed and are typically ground in grinding mills. Therefore, by ascertaining the metallic gloss of a coating from a coating composition while it is being made, the amount of flattener to be added to the mix can be adjusted in real time during the manufacture to finally attain coating compositions that would provide a desired metallic gloss.

A gloss of a layer from a coating composition in its wet state when measured directly can correlate to the metallic gloss that can result when such a layer dries and/or cures into a coating. However, since the optically proprieties of a wet layer of a coating composition continuously changes due to evaporation of solvent from and/or crosslinking of the wet layer, it is very difficult to correlate such wet optical property measurements to the metallic gloss of a coating that results from such a layer once it dries and/or cures into a coating. The process and the device of the present invention provide a solution to attaining the aforedescribed correlation.

Figure 1:
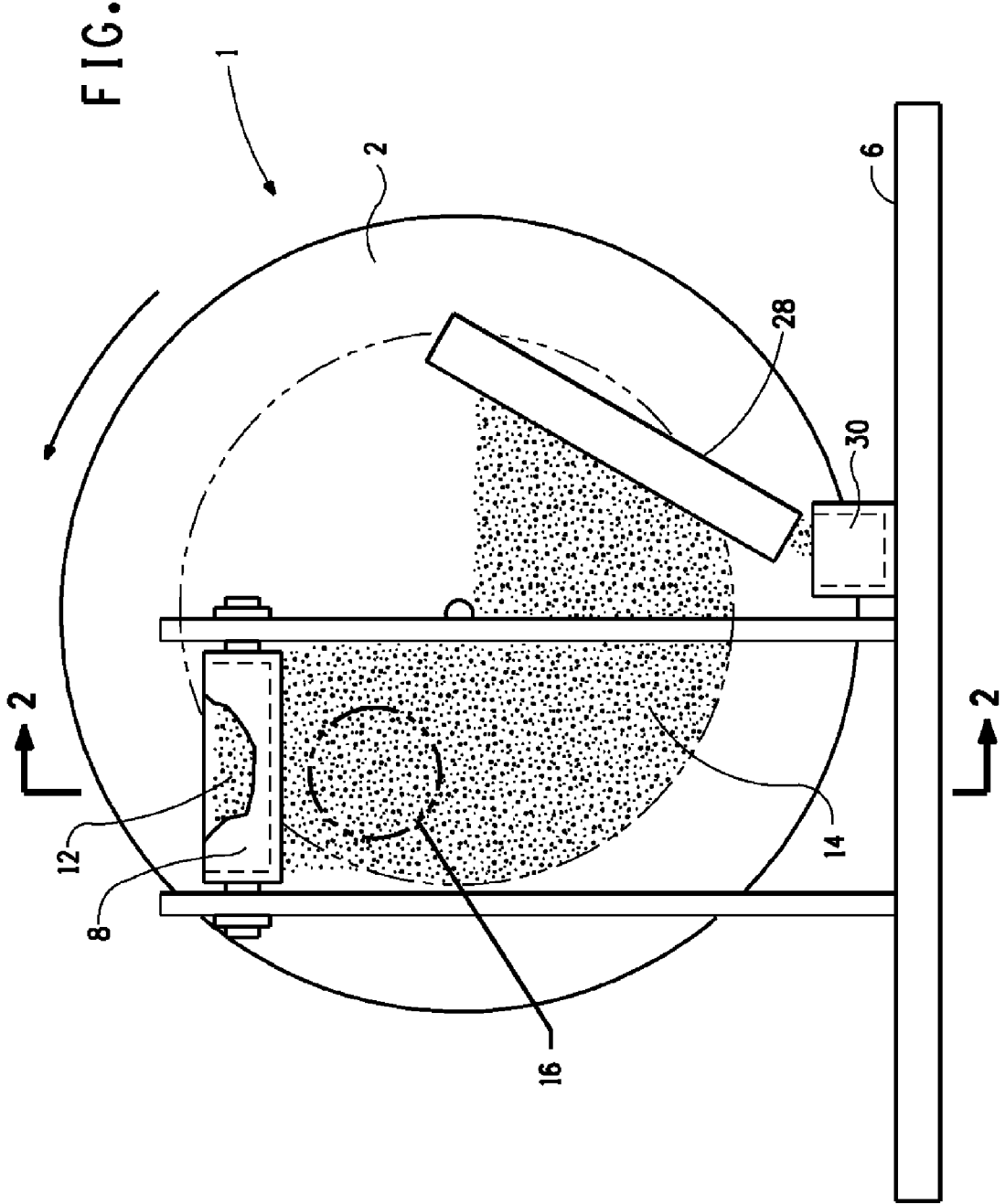
FIGS. 1 and 2 broadly illustrate one of the embodiments of a metallic gloss prediction device of the present invention.
Figure 2:
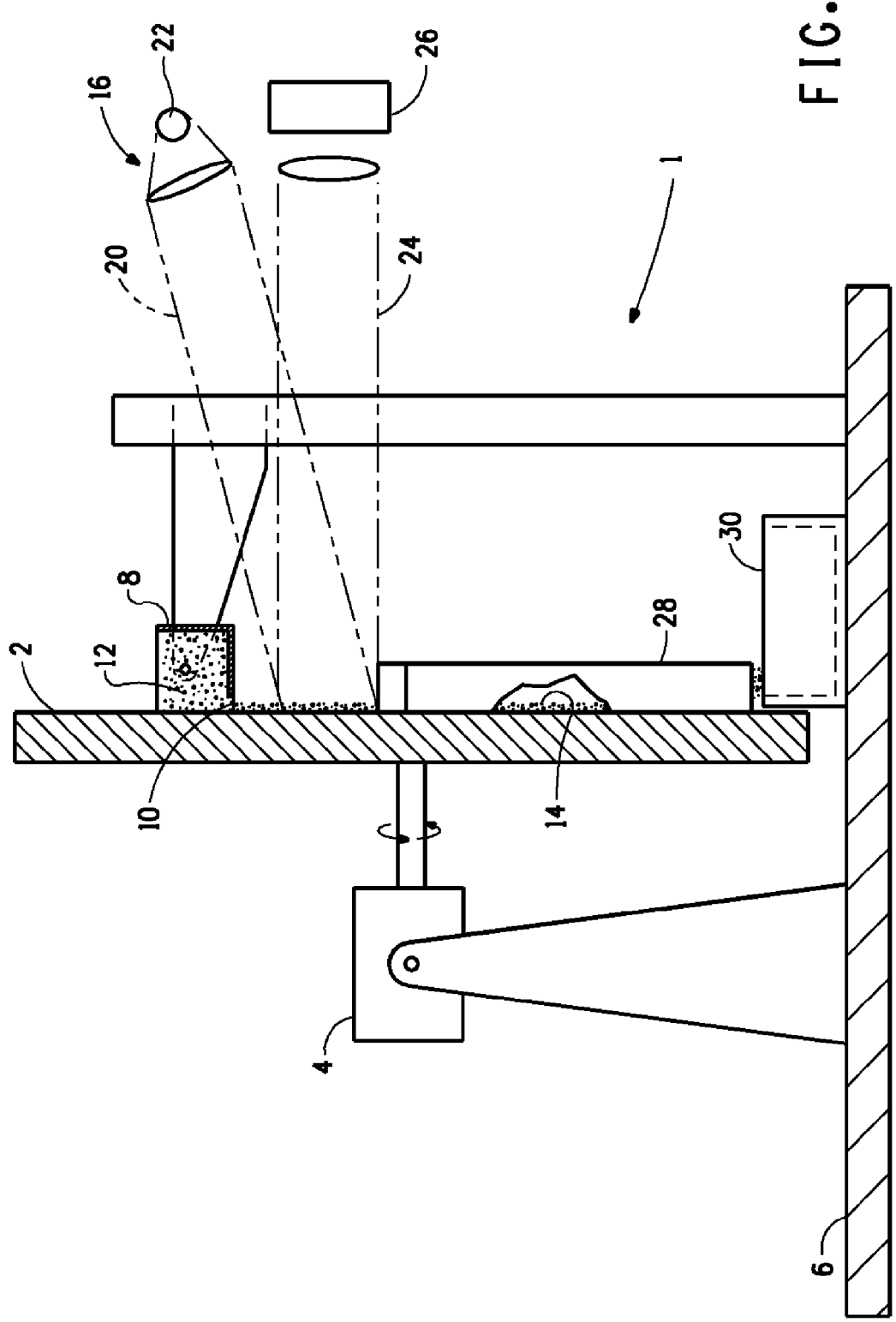

One of the gloss prediction devices suitable for the process of the present invention includes a device 1 shown in FIGS. 1 and 2. Device 1 includes a test substrate 2, preferably a disc, rotated by a driver 4, such as an electric motor, which is positioned on a support frame 6. Test substrate 2 mounted on a shaft of driver 4 can be positioned either in a horizontal or in a vertical position. Test substrate 2 of device 2 shown in FIGS. 1 and 2 is positioned vertically, which is preferred. Test substrate 2 can be made of any suitable material, such as steel, plastic or aluminum. The surface of test substrate 2 preferably has the same degree of smoothness as that of, for example, auto body or auto bumper such that the results obtained are as close to those that would have been obtained under the similar paint application conditions.

As shown in FIG. 1, Device 1 is provided with a vessel 8 positioned adjacent to test substrate 2. Vessel 8 is provided with an opening 10, preferably a slot, through which a coating composition ($S_0$) 12, when poured into vessel 8, can be applied as a $L_0$ layer 14 of a substantially uniform thickness on a measurement area 16 on the surface of test substrate 2. Coating composition ($S_0$) 12 used in producing $L_0$ layer 14, contains $F_0$ parts by weight of one or flatteners based on 100 parts by weight of coating composition ($S_0$) 12. Preferably, $S_0$ coating composition does not contain any flatteners. As test substrate 2 is rotated by driver 4, preferably for about a quarter turn, $L_0$ layer 14 is created. Opening 10 is adjacent to substrate 2 such that a resulting gap between opening 10 and substrate 2 controls the thickness of $L_0$ layer. Typically, $L_0$ layer is provided with a thickness that can range from 6 micrometers to 2300 micrometers.

Metallic gloss prediction device 1 of the present invention includes a conventional optical measurement mechanism 16 provided with conventional collimators for producing a beam of light 20 of preset intensity at a preset angle that can be projected on measurement area 16 from a conventional light source 22. A conventional optical measurement instrument typically measures conventional L,a,b color data on the reflectance of a surface color wherein L factor refers to lightness or darkness, "a" factor refers to (+a) redness to greenness (−a) and "b" factor refers to (+b) yellowness to blueness (−b). The applicants have unexpectedly discovered that the use of data from "L" value reported as ("B reflectance" above) results in the closest curve fitting of the data. Any angle of incidence and reflectance can be used. However, a 115 degree angle of reflectance (high observer) is typically employed and B reflectance is preferably measured before there is substantial change in the optical characteristics of $L_0$ layer 14 that depend on the physical and chemical properties of the coating composition from which $L_0$ layer 14 is produced. Thus, the higher the content of the solvent in the coating composition, the longer would be the window during which the reflectance can be measured and vice versa. Coating compositions that are lacquers (those containing high molecular weight non-reactive binder polymers dissolved in a solvent) typically would have longer measurement window than coating compositions that are enamels (those containing binder polymers containing reactive groups that chemically react with crosslinking groups on crosslinking agents that are mixed before being applied as a layer on a substrate). Typically, the reflectance is measured within 2 seconds to two minutes after $L_0$ layer 14 is applied over test substrate 2. A $B_0$ reflectance 24 of beam of light 20 off of $L_0$ layer 14 can then be measured by a conventional optical measurement instrument 26, such as MA-68 gloss measurement device supplied by X-Rite of Grand rapids, Mich. Typically, the gloss is measured within 2 seconds to two minutes after $L_0$ layer 14 is applied over test substrate 2.

After the measurement of reflectance, $L_0$ layer 14 is allowed to dry and/or cure into a $C_0$ coating and its $Y_0$ gloss is measured by means of a gloss meter (not-shown in FIG. 1) at a preset gloss angle, which is preferably 60 degrees. Generally, $Y_0$ gloss is measured within 4 hours to 48 hours, preferably within 6 hours to 24 hours, after coating composition 12 is applied over substrate 2. Typically, the time required for $L_0$ layer 14 to dry and/or cure depends upon the chemical make of the coating composition and typically an activator also know as crosslinking agent would be during the curing step when the coating composition is on the form of enamel.

Means for configuring computer readable program code devices is used to cause a conventional computer to store $B_0$ reflectance 24 of $L_0$ layer 14 and $Y_0$ gloss in a computer usable storage medium of the computer (not-shown in FIG. 1). The computer is preferably in communication with optical measurement instrument 26 and the gloss meter. If desired, the computer can be in communication with a remote computer, such as an offsite computer used to gather information from one or more computers connected to gloss prediction devices of the present invention.

If desired, after $Y_0$ gloss of $C_0$ coating is measured, substrate 2 can be rotated further by driver 4 to scrape off $C_0$ coating 14 with a doctor blade 28 into a waste container 30 and substrate 2 can then be cleaned. Alternatively, substrate 2 can be removed and $C_0$ coating scraped off substrate 2 and which is then cleaned.

The aforedescribed procedure is then repeated with series of $S_1, S_2, \ldots S_n$ (n being in the range of 1 to 100, preferably from 2 to 50 and more preferably from 5 to 20) coating compositions 12 containing increasing amounts flatteners ranging from $F_1$ to $F_n$ weight parts per 100 weight parts of coating composition. One or more flatteners added to the coating composition can be preferably increased in suitable incremental amounts, such as 0.001, 0.01, 0.1, 0.5, 1, 5, 10, 15 weight parts in per 100 weight parts of the coating composition, with $F_1$ preferably ranging from 0.001 weight part to 5 weight parts per 100 weight parts of the coating composition and $F_n$ preferably ranging from 5.1 weight parts to 60 weight parts per 100 weight parts of coating composition. As described above, $B_1$ reflectance 24 from a $L_1$ layer 14 from $S_1$ coating composition and $Y_1$ gloss of $C_1$ coating is measured and the means for configuring computer readable program code devices is used to cause the computer to store $B_1$ reflectance 24 of $L_1$ layer 14 and $Y_1$ gloss of $C_1$ coating in the computer usable storage medium of the computer. The process is repeated until $B_n$ reflectance from a $L_n$ layer 14 and $Y_n$ gloss of $C_n$ coating from coating composition $12_n$ is measured and stored in the computer usable storage medium of the computer.

Alternatively, a duplicate of $L_0$ layer 14 is allowed to dry and/or cure into a $C_0$ coating and its $Y_0$ gloss is measured by means of a gloss meter (not-shown in FIG. 1) at a preset gloss angle, which is preferably 60 degrees. Generally, $Y_0$ gloss is measured within 4 hours to 48 hours, preferably within 6 hours to 24 hours, after coating composition 12 is applied over substrate 2. The aforementioned duplicate layer of $L_0$ layer 14 can be applied on another similar substrate including a glass substrate by suitable means such as doctor blade.

The means for configuring computer readable program code devices is used to cause the computer to locate intersecting points on a graph where $B_0$ to $B_n$ reflectances of $L_0$ to $L_n$ layers 14 on X-axis of the graph intersect with the $Y_0$ to $Y_n$ metallic gloss of $S_0$ to $S_n$ coatings, respectively based on $S_0$ to $S_n$ coating compositions, on Y-axis of the graph. The means for configuring computer readable program code devices is then used to cause the computer to use a curve fitting equation to produce a metallic gloss prediction curve on the graph. Preferably, the curve fitting equation is a second degree polynomial equation. More preferred second degree polynomial equation is of the following formula:

$$\text{Gloss } Y=a(B_n)^2+b(B_n)+c \quad (1)$$

$$R^2=Z \quad (2)$$

wherein said constants a, b, c and $R^2$ are determined by a curve fitting process, such as that described in Microsoft Office Excel® 2003 supplied by Microsoft Corporation of Redmond, Wash. Z is a statistical measure of how close the curve fits to the experimental datum points on a graph. When Z is equal to 1, it is considered to be an ideal fit, i.e., all the experimental datum points lay on the fitted curve. All the necessary and relevant information is stored on the computer usable storage medium.

If desired, the metallic gloss prediction curve on the graph may be displayed on a conventional monitor and/or printed on paper by means of a conventional printer both of which being in communication with the computer. Once the metallic gloss prediction curve on the graph is produced, the user can use the gloss prediction device of the present invention to control the metallic gloss of a target coating composition containing an unknown or known amount of flatteners without going through the cumbersome and time consuming process of curing the layer into a coating. $L_T$ layer 14 (also know as target layer) from the target coating composition, preferably having the same substantially uniform thickness as the layers used in creating the metallic gloss prediction curve, dispensed over substrate 2 of metallic gloss prediction device 1 of the present invention can be used in a production set up that allows the manufacturer of a coating composition to expeditiously adjust the ingredients of the coating composition for ensuring that the resulting coating composition has a desired degree of metallic gloss.

As described above, $B_T$ reflectance 24 from $L_T$ layer 14 from the target coating composition is measured and the means for configuring computer readable program code devices is used to cause the computer to store $B_T$ reflectance 24 of $L_T$ layer 14 in the computer usable storage medium of the computer.

The means for configuring computer readable program code devices is then used to cause the computer to locate $B_T$ reflectance of $L_T$ layer on the X-axis of the graph. The means for configuring computer readable program code devices is used to cause the computer to locate an intersecting point on the metallic gloss prediction curve that intersects with $B_T$ on X-axis of the graph. Finally, The means for configuring computer readable program code devices is used to cause the computer to predict the metallic gloss of a target coating resulting from $L_T$ layer by locating $Y_T$ gloss on the Y-axis of the graph that intersects with the intersecting point on the flake amount prediction curve that intersects with $B_T$ on the X-axis of the graph.

As a result, once the metallic gloss prediction curve is stored in a computer of device 1, an aliquot of a coating composition being made can be applied as a layer and its wet gloss measured to predict the metallic gloss of a coating resulting from said composition. If the metallic gloss falls outside of desired specification, the manufacturing process can be adjusted in real time without interruption by monitoring and adjusting the amount the flattener added on a contenting basis.

Few of the aspects of the aforedescribed metallic gloss prediction device 1 of the present invention are described in German patent application DT 25 25 701 A1. It should be understood that substrate 2 need not be positioned vertically or have to have a disc shape. Other embodiments, such as those where substrate is positioned horizontally, or is in the form of a belt, etc. are also well suited for the process of the present invention. For example, substrate in the form of a roller, as described in a commonly assigned U.S. Pat. No. 6,583,878 to Hustert, is also well suited for the process of the present invention.

One embodiment of the process of the present invention utilizes metallic gloss prediction device 1 of FIG. 1. The process includes dispensing on substrate 2, $L_0$ layer 14 of a substantially uniform thickness of coating composition 12 through vessel 8, which contains coating composition 12. Then beam of light 20 of a preset intensity at a preset angle of incidence from light source 22 is projected on measurement area 16 of $L_0$ layer. By means of optical measurement instrument 26, $B_0$ reflectance of beam of light 20 is measured at a preset angle of reflectance. $L_0$ layer is dried and/or cured into $C_0$ coating and $Y_0$ gloss of $C_0$ coating at a preset angle is measured by gloss meter. $B_0$ reflectance of $L_0$ layer and $Y_0$ gloss of $C_0$ coating are then stored in the computer usable storage medium of the computer. The aforedescribed steps are repeated for $S_1$ to $S_n$ coating compositions 12 further comprising $F_1$ to $F_n$ parts by weight of one or more flatteners based on 100 parts by weight of the coating composition respectively to determine $B_1$ to $B_n$ reflectance of $L_1$ to $L_n$ layers and $Y_1$ to $Y_n$ gloss of $C_1$ to $C_n$ coatings, respectively wherein n ranges from 1 to 100.

EXAMPLES

Table 1 below lists coating composition samples which include increasing amounts (parts by weight) of flattener (TUG09-GC01 Flattener supplied by DuPont Company of Wilmington, Del.) were mixed with a pot mix containing 20 parts by weight of EcoMax™ Silver TU109-4003 enamel, wherein Example 1 contained no flattener. Layers of these Examples 1 though 5 were applied over substrate 2 of Device 1 and the reflectances of the layers were measured by using MA-68 color instrument 26 supplied by X-Rite of Grand Rapids, Mich. at 115 degrees and the L-value from those reflectances was reported. To each of Examples 1 through 6, TU09AS activator supplied by DuPont Company of Wilmington, Del. was added at 2:1 volumetric ratio and duplicate layers substantially same as those produced over substrate 2 of Device 1 were applied with doctor blade over glass substrate and 24 hours at 20 C and 50% humidity, metallic gloss of the corresponding coatings resulting from these Examples were measured at 60 degrees by means of Haz-Gloss Meter supplied by BYK Instruments of Columbia, Md.:

TABLE 1

|  | Ex. 1 | Ex. 2 | Ex. 3 | Ex. 4 | Ex. 5 |
|---|---|---|---|---|---|
| Wet $B_0$ reflectance (L-value) | 33.48 | 36.95 | 42.72 | 44.52 | 45.53 |
| Dry metallic gloss | 105 | 90 | 68 | 40 | 7.2 |

Figure 3:
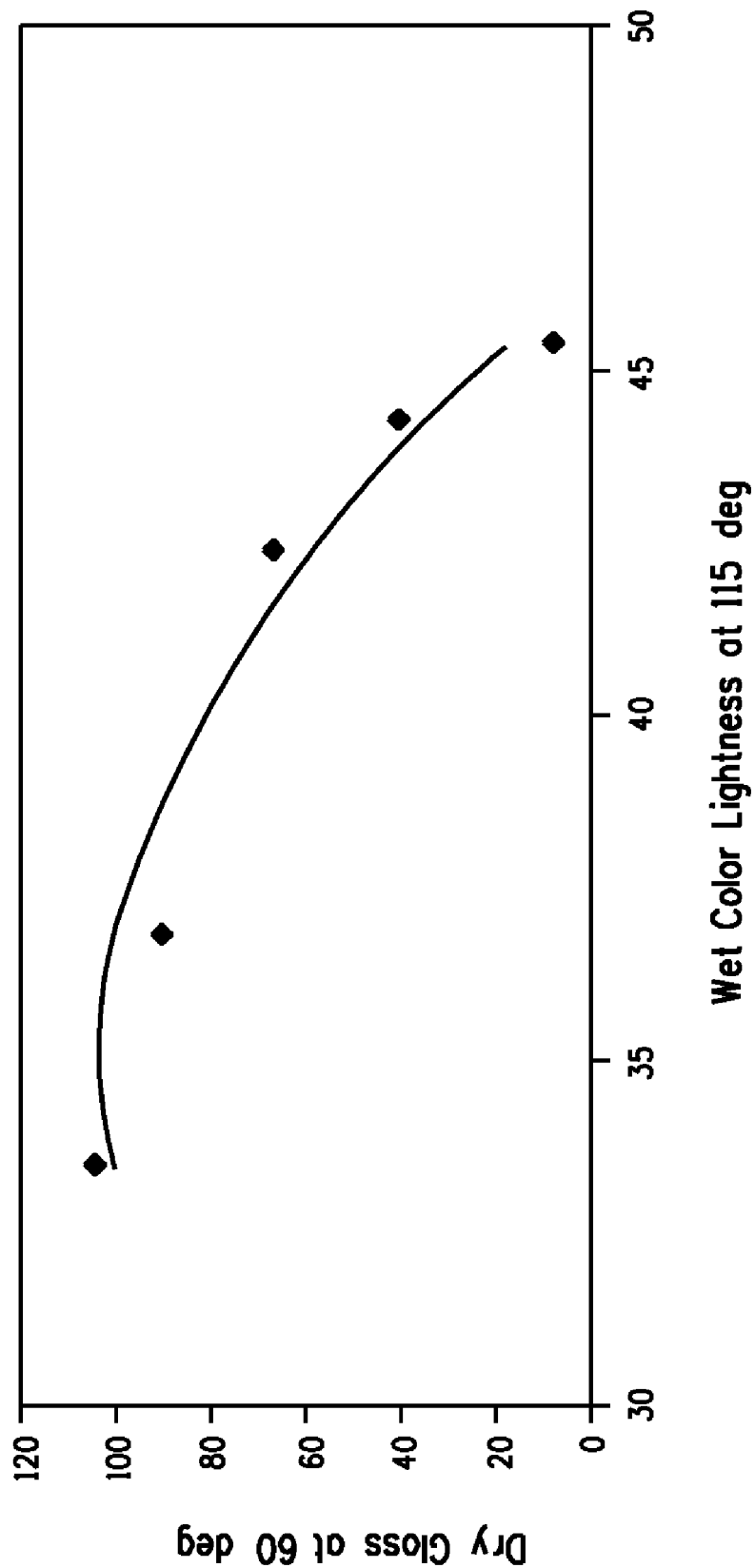
FIG. 3 broadly illustrates the metallic gloss prediction curve produced by a metallic gloss prediction process of the present invention.

As shown in FIG. 3, intersecting points on a graph where $B_0$ to $B_n$ of $L_0$ to $L_n$ layers on X-axis of the graph intersect with $F_0$ to $F_n$ amounts of coarse flakes of $S_0$ to $S_n$ coating compositions on Y-axis of the graph are then located.

Using a curve fitting equation, such as the aforementioned secondary degree polynomial equation (1) is then used to produce a metallic gloss prediction curve, such as that shown in FIG. 3. The term "a" in the equation (1) was −0.8291. The term "b" in the equation (1) was 58.655 and the term "c" in the equation was −934.34. The statistical measure Z was 0.9374. All of the foregoing terms were obtained by using the aforementioned Microsoft Excel® program. It would be readily to apparent to one of ordinary skill in the art that the statistical measure Z of 0.9374 indicates the curve of the metallic gloss prediction was a very close fit to the Z of the ideal fit of 1.

The process of the present invention is then used to predict the metallic gloss of a target coating composition by first dispensing on substrate 2 a $L_T$ layer of preferably the same substantially uniform thickness of a target coating composition through vessel 8 of metallic gloss prediction device 1 containing the target coating composition further comprising an unknown or a known amount of one or more flatteners. A beam of light 20 at the preset intensity and at the preset angle of incidence from light source 22 is then projected on measurement area 16 of $L_T$ layer and L value of $B_T$ reflectance of beam reflected from $L_T$ layer at the preset angle of reflectance is measured by optical measurement instrument 26. An intersecting point on the metallic gloss prediction curve that intersects with $B_T$ reflectance on the X-axis of said graph is then located and the metallic gloss at the preset gloss angle of a coating resulting from $L_T$ layer is then predicted by locating $Y_T$ on the Y-axis of the graph.

Thus, one of ordinary skill in the art can readily see that the metallic gloss of a coating can be readily predicted by the metallic gloss prediction curve of the process of the present invention by just measuring the gloss of a wet layer of a coating composition from which coating is produced.

The process and device of the present invention is most suitable for ensuring that the metallic gloss of automotive OEM and refinish paints resulting from coatings therefrom falls within a desired range.

What is claimed is:

1. A metallic gloss prediction process comprising:
(a) dispensing on a test substrate a $L_0$ layer of a substantially uniform thickness of a $S_0$ coating composition containing metallic flakes through a vessel of a metallic gloss prediction device containing said coating composition;
(b) projecting on said $L_0$ layer a beam of light of a preset intensity at a preset angle of incidence from a light source;
(c) measuring $B_0$ reflectance of said beam reflected from said $L_0$ layer at a preset angle of reflectance by an optical measurement instrument;
(d) curing or drying said $L_0$ layer into a $C_0$ coating;
(e) measuring $Y_0$ metallic gloss of said $C_0$ coating at a preset metallic gloss angle by a gloss meter;
(f) storing said $B_0$ reflectance of said $L_0$ layer and said $Y_0$ metallic gloss of said $C_0$ coating in a computer usable storage medium of a computer;
(g) repeating said steps (a) through (f) for $S_1$ to $S_n$ coating compositions respectively comprising $F_1$ to $F_n$ parts by weight of one or more flatting agents based on 100 parts by weight of said coating composition to determine $B_1$ to $B_n$ reflectance of $L_1$ to $L_n$ layers and $Y_1$ to $Y_{in}$ metallic gloss of $C_1$ to $C_n$ coatings wherein n ranges from 4 to 20;
(h) locating intersecting points on a graph where said $B_0$ to $B_n$ of said $L_0$ to $L_n$ layers on X-axis of said graph intersect with said $Y_0$ to $Y_n$ metallic gloss of said $C_0$ to $C_n$ coatings on Y-axis of said graph;
(i) using a curve fitting equation to produce a metallic gloss prediction curve on said graph;
j) dispensing on said test substrate a $L_T$ layer of said substantially uniform thickness of a target coating composition through said vessel of said metallic gloss prediction device containing said target coating composition further comprising said flatting agent;
(k) projecting on said $L_T$ layer a beam of light at said preset intensity and at said preset angle of incidence from said light source;
(l) measuring $B_T$ reflectance of said beam reflected from said $L_T$ layer at said preset angle of reflectance by said optical measurement device;
(m) locating said $B_T$ of said $L_T$ layer on said X-axis of said graph;
(n) locating an intersecting point on said metallic gloss prediction curve that intersects with said $B_T$ on said X-axis of said graph; and
(o) predicting metallic gloss at said preset metallic gloss angle of a target coating resulting from said target layer by locating $Y_T$ on said Y-axis of said graph that intersects with said intersecting point on said metallic gloss prediction curve that intersects with said $B_T$ on said X-axis of said graph.

2. The process of claim 1 wherein said optical measurement device is a spectrophotometer.

3. The process of claim 1 wherein said optical measurement instrument is in communication with said computer.

4. The process of claim 1 wherein said metallic gloss meter is in communication with said computer.

5. The process of claim 1 wherein said opening is a slot adjacent to said test substrate such that a resulting gap between said slot and said test substrate controls the thickness of said $L_0$ and said $L_1$ to $L_n$ layers.

6. The process of claim 1 wherein said $L_0$ and said $L_1$ to $L_n$ layers are of the same thickness ranging from 6 micrometers to 2300 micrometers.

7. The process of claim 1 wherein said test substrate is a disc positioned substantially vertically on a support frame of said metallic gloss prediction device.

8. The process of claim 1 wherein said curve fitting equation is a second degree polynomial equation.

9. The process of claim 8 wherein said second degree polynomial equation is of the formula:

Metallic gloss $Y=a(B_n)^2+b(Bn)+c$ $R^2=Z$ wherein constants a, b, c and $R^2$ are determined by a curve fitting process.

10. The process of claim 1 comprising displaying said predicted metallic gloss of said target coating on a CRT monitor.

11. The process of claim 1 comprising communicating said predicted metallic gloss of said target coating from said computer to a remote computer.

12. The process of claim 1 wherein said coating composition is an automotive original equipment manufacturer or refinish paint.

13. The process of claim 12 wherein said flatting agent is talc, silica, or barium sulfate.

14. The process of claim 1 wherein said metallic flakes are aluminum flakes, mica flakes, inorganic flakes, organic flakes or a combination thereof.

* * * * *